US009694145B1

(12) United States Patent
Onorato (10) Patent No.: US 9,694,145 B1
(45) Date of Patent: Jul. 4, 2017

(54) AUTO-INJECTOR SYSTEMS AND METHOD FOR DELIVERING CYST MEDICATION ON DEMAND

(71) Applicant: Joseph Onorato, Oyster Bay, NY (US)

(72) Inventor: Joseph Onorato, Oyster Bay, NY (US)

( * ) Notice: Subject to any disclaimer, the term of this patent is extended or adjusted under 35 U.S.C. 154(b) by 0 days.

(21) Appl. No.: 15/240,679

(22) Filed: Aug. 18, 2016

Related U.S. Application Data (60) Provisional application No. 62/314,616, filed on Mar. 29, 2016.

(51) Int. Cl.
  *A61M 5/00* (2006.01)
  *A61M 5/46* (2006.01)
  *A61M 5/42* (2006.01)
  *A61M 5/24* (2006.01)
  *A61M 5/315* (2006.01)

(52) U.S. Cl.
  CPC ............... *A61M 5/46* (2013.01); *A61M 5/24* (2013.01); *A61M 5/3153* (2013.01); *A61M 5/3155* (2013.01); *A61M 5/3159* (2013.01); *A61M 5/31593* (2013.01); *A61M 5/42* (2013.01); *A61M 2210/04* (2013.01)

(58) Field of Classification Search
  CPC .......... A61M 5/31533; A61M 5/31545; A61M 5/31546; A61M 5/31548; A61M 5/3155; A61M 5/31551; A61M 5/31553; A61M 5/31555; A61M 5/3156; A61M 5/31561; A61M 5/31563; A61M 5/46
  See application file for complete search history.

(56) References Cited

U.S. PATENT DOCUMENTS

| | | | |
|---|---|---|---|
| 2,565,081 A * | 8/1951 | Maynes | A61M 5/2033 604/136 |
| 5,034,002 A | 7/1991 | Duranzampa et al. | |
| 5,042,977 A * | 8/1991 | Bechtold | A61M 5/20 604/134 |
| 5,104,380 A | 4/1992 | Holman et al. | |
| 5,256,140 A | 10/1993 | Fallick | |
| 5,480,387 A * | 1/1996 | Gabriel | A61M 5/20 604/134 |
| 6,171,276 B1 * | 1/2001 | Lippe | A61M 5/20 128/DIG. 1 |
| 6,203,530 B1 | 3/2001 | Stewart, Sr. | |
| 6,790,456 B2 | 9/2004 | Vogel et al. | |
| 7,442,185 B2 | 10/2008 | Amark et al. | |
| 8,123,724 B2 | 2/2012 | Gillespie, III | |
| 8,128,960 B2 | 3/2012 | Kabra et al. | |

(Continued)

*Primary Examiner* — Kevin C Sirmons
*Assistant Examiner* — William Carpenter
(74) *Attorney, Agent, or Firm* — Michele V. Frank; Venable LLP (57) ABSTRACT

An auto-injector device including a syringe, a needle arranged in the vicinity of a first end of the syringe, and a plunger arranged within the syringe. A volume within the syringe between the plunger the needle accommodates medicine, such that movement of the plunger toward the needle dispenses medicine through the needle. A selection assembly configurable by a user to adjust an amount of medicine dispensed by the auto-injector device and depth to which the medicine is delivered. Also, a method for treating a skin lesion or skin disorder utilizing the auto-injector and a kit for patient administered treatment.

18 Claims, 8 Drawing Sheets

(56) References Cited

U.S. PATENT DOCUMENTS

| | | | |
|---|---|---|---|
| 2003/0040716 A1* | 2/2003 | Heiniger | A61M 5/3257 604/197 |
| 2004/0225276 A1 | 11/2004 | Burgess | |
| 2012/0056019 A1* | 3/2012 | Renz | A61M 5/2033 239/584 |
| 2014/0336577 A1 | 11/2014 | McCoy | |

* cited by examiner

AUTO-INJECTOR SYSTEMS AND METHOD FOR DELIVERING CYST MEDICATION ON DEMAND

CROSS-REFERENCE TO RELATED APPLICATIONS

This application claims priority to U.S. provisional patent application 62/314,616, filed Mar. 29, 2016, the entire contents of the disclosure of which are hereby incorporated by reference.

TECHNICAL FIELD

The present invention relates to an auto-injection device that is configurable by a patient to administer varying doses of a medicine. The invention also relates to a method for a patient to configure an auto-injection device and administer a particular dose of medicine and operating the auto-injection device to administer the dose of medicine. In particular the method relates to self-treatment of by a patient of acne cysts.

BACKGROUND

All aspects of medical practice continue to change at a rapid pace. In fact, everything from insurance to new drugs and medical devices to the nature of the doctor-patient relationship is changing. Additionally, prevalent advertising by pharmaceutical companies makes patients aware of the latest developments in drugs. Furthermore, the internet has made information widely available.

In some ways, the changes may be good. For example, the internet can provide almost instantaneous access to patient records for both physicians and patients. On the other hand, the internet permits dissemination of massive amounts of erroneous medical information. Other changes are negative. For example, decreased reimbursement rates and rising costs, such as for medical malpractice insurance, create great pressures on profitability.

In some ways, these changes are interrelated and can provide benefits to both physicians and patients. For example, patient access to medical records can reduce staff time responding to patient inquiries. The internet and telephone may provide benefits beyond dissemination of information. For example, physicians and other providers may interact with patients on the telephone to diagnose conditions. Additionally, the internet may be utilized to send photos or videos relevant to conditions.

BRIEF SUMMARY OF THE INVENTION

Embodiments of the invention include an auto-injector device. The device includes a syringe. A needle is arranged in the vicinity of a first end of the syringe. A plunger is arranged within the syringe. A volume within the syringe between the plunger and the needle accommodates medicine, such that movement of the plunger toward the needle dispenses medicine through the needle. A selection assembly is configurable by a patient to adjust an amount of medicine dispensed by the auto-injector device and depth to which the medicine is delivered.

Other embodiments of the invention include method for self-administration of medicine by a patient. The patient measures a size of a cyst on a skin surface of the patient. The patient configures a selection assembly of an auto-injector to administer a dose of medicine including an amount of medicine based on the size of the cyst. The patient administers the medicine by causing a plunger of the auto-injector to advance through a syringe of the injector.

Still other objects and advantages of the present invention will become readily apparent by those skilled in the art from the following detailed description, wherein is shown and described only the preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the drawings and description are to be regarded as illustrative in nature and not as restrictive.

BRIEF DESCRIPTION OF THE DRAWINGS

The above-mentioned objects and advantages of the present invention will be more clearly understood when considered in conjunction with the accompanying drawings, in which.

DETAILED DESCRIPTION OF THE INVENTION

Effective and timely treatment at reduced cost would be an ideal scenario. Patient self-administration may be one element that could help achieve such a goal. Additionally, unlike in the past where remote interactions between physicians and patients included only voice communication through the telephone, the internet can permit the transmission of documents, photos and video. Ease of transmission of information may also facilitate medical care.

Effective self-administration of medication may be enhanced by simplifying the administration technique. For example, a great deal of time was expended to simplify instructions for automatic external defibrillators to help ensure that patients could easily and effectively use them. Additionally, the adaptability of the administration technique to multiple conditions may further enhance the effectiveness of self-administration of medication.

The auto-injector could be prescribed or provided to patients during an office visit. The patient could take the auto-injector home or pick it up from a pharmacy to have when needed. Alternatively, the patient could fill the prescription when needed. Additionally, a patient could contact a physician, nurse practitioner, physician's assistant, nurse or other provider, over the telephone, through e-mail or other means, discuss the patient's condition and possibly view photos or video of the patient's condition. The auto-injector could be prescribed to a patient without an office visit.

Eliminating an office visit could eliminate the need for an appointment, saving time. In fact, a patient could obtain an auto-injector to have at home or when away from home, such as at school, work or on a business or leisure trip. Additionally, eliminating the need for an appointment could eliminate the need for a referral and a co-pay. Perhaps most importantly, the patient can achieve immediate treatment upon developing any one of a number of conditions.

A variety of conditions may be self-treated by patients utilizing the auto-injector. For example, an acne cyst, such a cyst anywhere on the body or an inflamed acne cyst. Additionally, inflamed sebaceous cysts, bug bites, erythema nodusum, alopecia areata, hypertrophic scars, keloids, granuloma annulare, discoid lupus erythematosus, hypertrophic lichen planus, lichen planopilaris, lichen simplex chronicus, psoriasis, sarcoidosis, prurigo nodularis, viral warts, vascular anomalies, carcinomas, karatoacanthomas, Kaposi sarcoma, lupus erythematosus, sarcoidosis, lentigo maligna, Peyronie's disease, and genital warts are among the conditions that could be treated. Immediate treatment could greatly speed recovery time. For example, a condition could be resolved in one day.

Such conditions typically involve a lesion. The lesion may be generally round. Typically, the lesions are generally circular, papules or nodules, elevated bumps or lumps. Such lesions may be inflammatory in nature. Rather than being round, the lesions could be linear, curvilinear, or annular. A plurality of lesions could be arranged in a linear, curvilinear or annular pattern. Lesions may also not result from inflammatory processes. Additionally, the lesions may not be raised and could have other shapes.

As described below in greater detail, the auto-injector not only permits patient self-administration, a patient may control dose administered by the auto-injector, thereby increasing the potential of the auto-injector to save money. Along these lines, the auto-injector may be able to treat lesions and skin disorders of different sizes and a vast number of dermatological and other conditions. Currently, patients must make an appointment, perhaps obtain pre-authorization for a specialist visit, take time to travel to the physician's office, wait in the office and then have a cyst injected with medication. The auto-injector has the possibility to revolutionize treatment in many ways, including savings of time and money.

Figure 1:
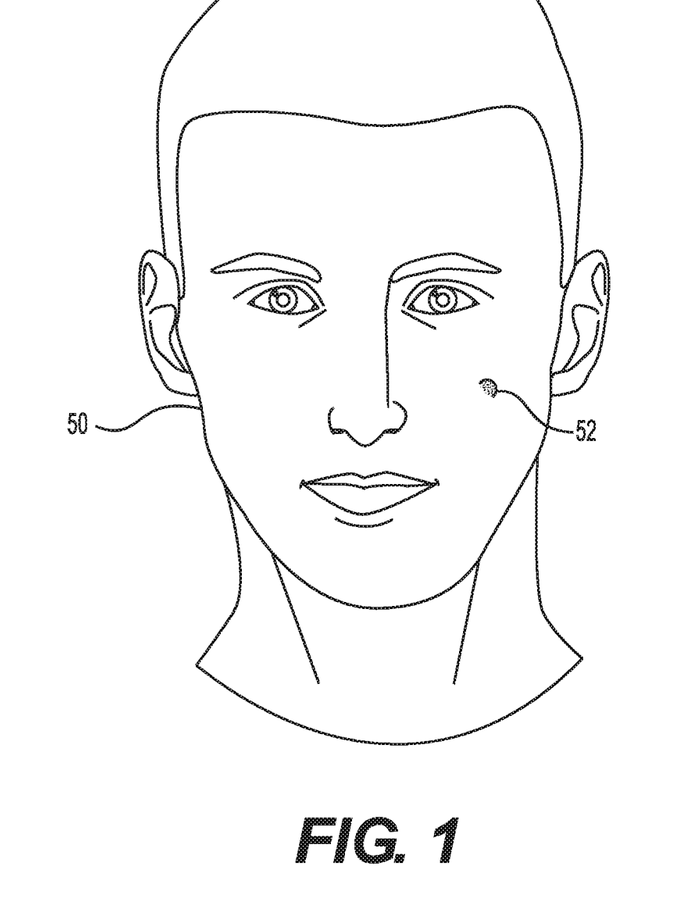
FIG. 1 represents a patient with an inflamed lesion or other skin disorder.
Figure 2:
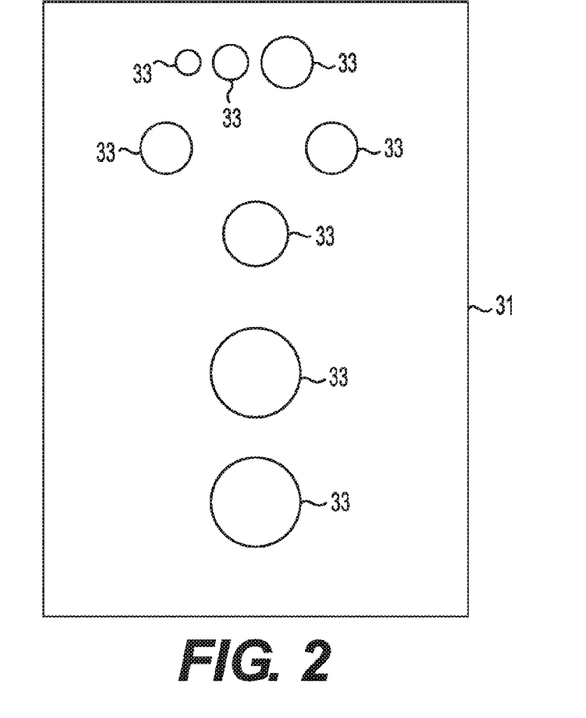
FIG. 2 represents an embodiment of a measuring grid that may be utilized with the auto-injector to measure diameter and height of a lesion or other skin disorder.
Figure 3:
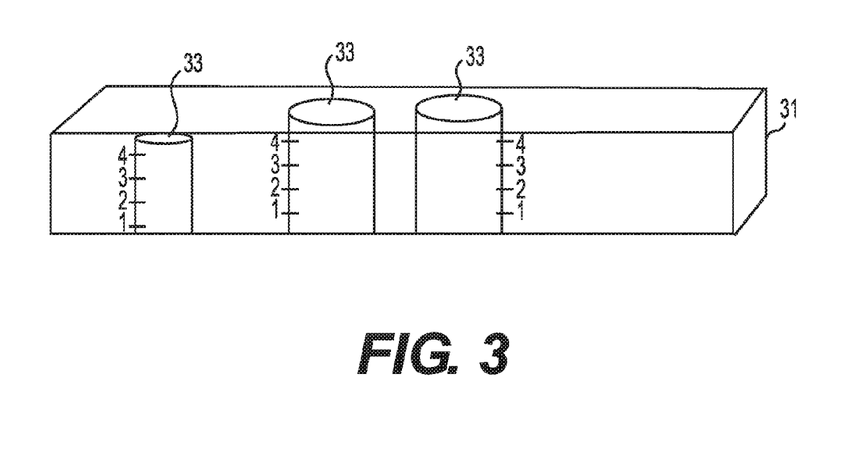
FIG. 3 represents a side view of the embodiment of the measuring grid shown in FIG. 2.

FIG. 1 illustrates a patient 50 with an inflamed lesion or other skin disorder 52. When a lesion is identified for treatment, typically, the lesion is measured to help ensure that a correct dosage of medicine is administered. The diameter and/or the height of the lesion may be measured. This may be carried out utilizing a ruler or other measuring device. According to one embodiment, evaluation of a lesion for proposed dose and depth of medicant may be carried out utilizing a measuring grid. FIGS. 2 and 3 illustrate an embodiment of a measuring grid 31 that may be utilized to measure a lesion. This embodiment of the measuring grid includes a plurality of holes to measure different size lesions. The size of the openings in the measuring grid may vary depending at least in part upon the cause of the lesion-some conditions tend to generate large lesions and some small.

Typically, a measuring grid includes a plurality of openings of different sizes. The embodiment shown in FIGS. 2 and 3 includes openings 33 having diameters of about 6 mm, 8 mm, 10 mm, 12 mm, 14 mm, 15 mm, 20 mm, or 25 mm. The openings may be placed over the lesion or disorder to determine the size of the lesion or skin disorder. As shown in FIG. 3, the measuring grid may also be utilized to measure the height of a lesion. For example, the holes in the grid may include markings that permit measuring the height. The grid may be placed on the lesion and the depth viewed from the side, if the grid is made of a clear material, or by viewing how far the lesion extends up the side of an opening.

Once the size of the lesion or other skin disorder is determined, the correct size injection guide and depth may be secured to the auto-injector or auto-injector including a correct sized injection guide may be selected. The auto-injector may then be positioned over the lesion and the injection carried out. Placing the measuring grid on the lesion for diameter will determine the dose. Table 1 below provides examples of diagnoses, the type of process that results in the lesion, and how depth and dose are determined.

TABLE 1

| DIAGNOSIS | Type of Process (Lesion or Disorder) | Dose (determined by Diameter or Provider) | Depth (determined by Height or Provider |
|---|---|---|---|
| Acne Cysts | Lesion | Diameter | Height |
| Inflamed Sebaceous Cyst | Lesion | Diameter | Height |
| Bug Bites | Lesion | Diameter | Height |
| Alopecia Areata | Disorder | Provider | Provider |
| Hypertrophic Scars | Disorder | Provider | Provider |
| Keloids | Disorder | Provider | Provider |
| Psoriasis | Disorder | Provider | Provider |
| Granuloma Annulare | Disorder | Provider | Provider |
| Discoid Lupus Erythematosus | Disorder | Provider | Provider |
| Hypertrophic Lichen Planus | Disorder | Provider | Provider |
| Lichen Planopilaris | Disorder | Provider | Provider |
| Lichen Simplex Chronicus | Disorder | Provider | Provider |
| Erythema Nodosum | Disorder | Provider | Provider |
| Sarcoidosis | Lesion | Diameter | Height |
| Prurigo Nodularis | Lesion | Diameter | Height |

Evaluation of a disorder for proper dose and depth of medicant may be determined by a healthcare provider, such as a physician, physician assistant, or nurse practitioner. A disorder of the skin may be treated intralesionally (in the lesion) or intradermally (in the skin). That is, if the inflammation is in the dermis the treatment will be intradermally. On the other hand, if the inflammation is above the level of the skin then the treatment will be intralesionally. The provider may determine the thickness and body area of an inflammatory skin disorder and then choose the proper depth and dose of the medicant. Thickness of the dermis varies from about 0.6 mm to about 3 mm, depending on the body area. The face has the thinnest dermis (0.6 mm) and the back has the thickest dermis (3 mm).

Figure 4:
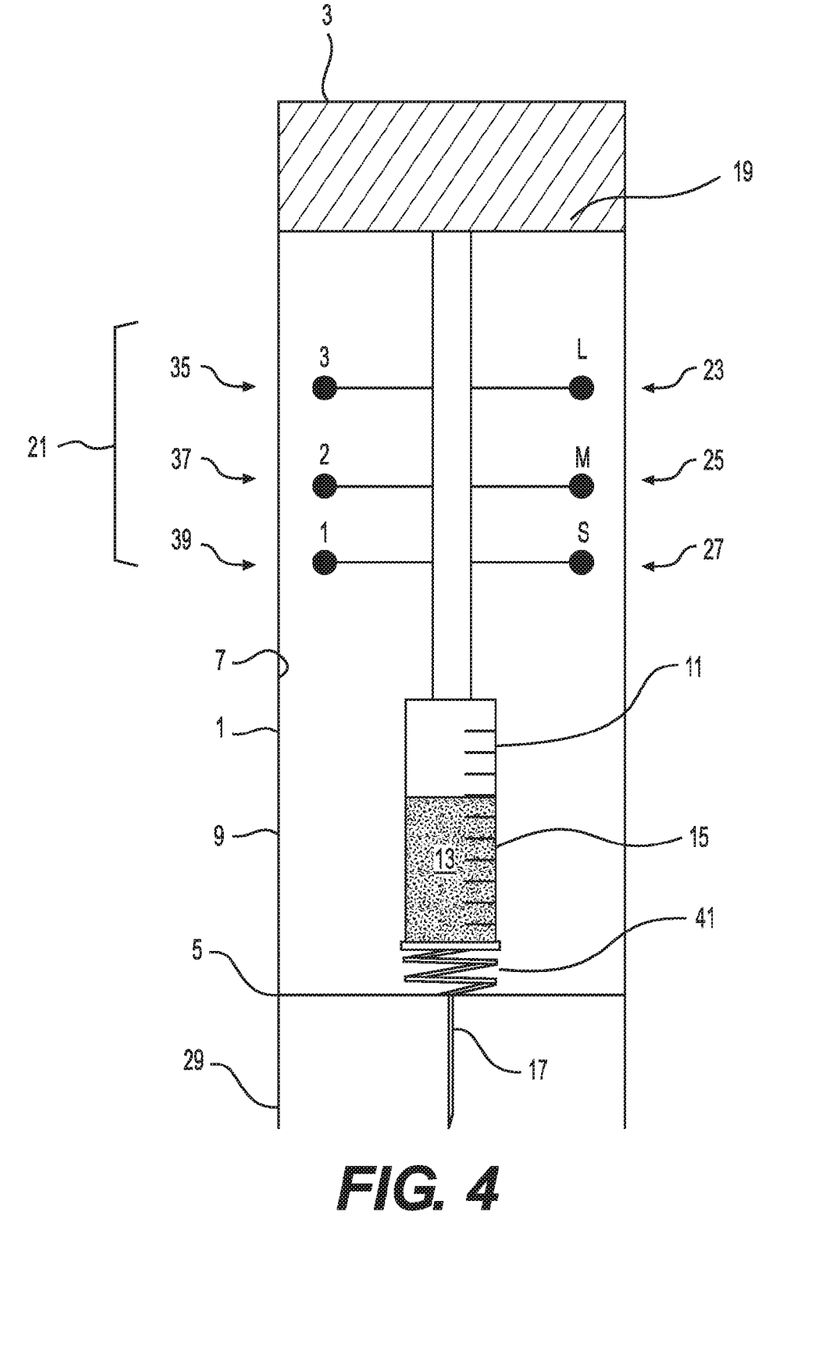
FIG. 4 represents a cross-sectional view of an embodiment of an auto-injector.
Figure 5:
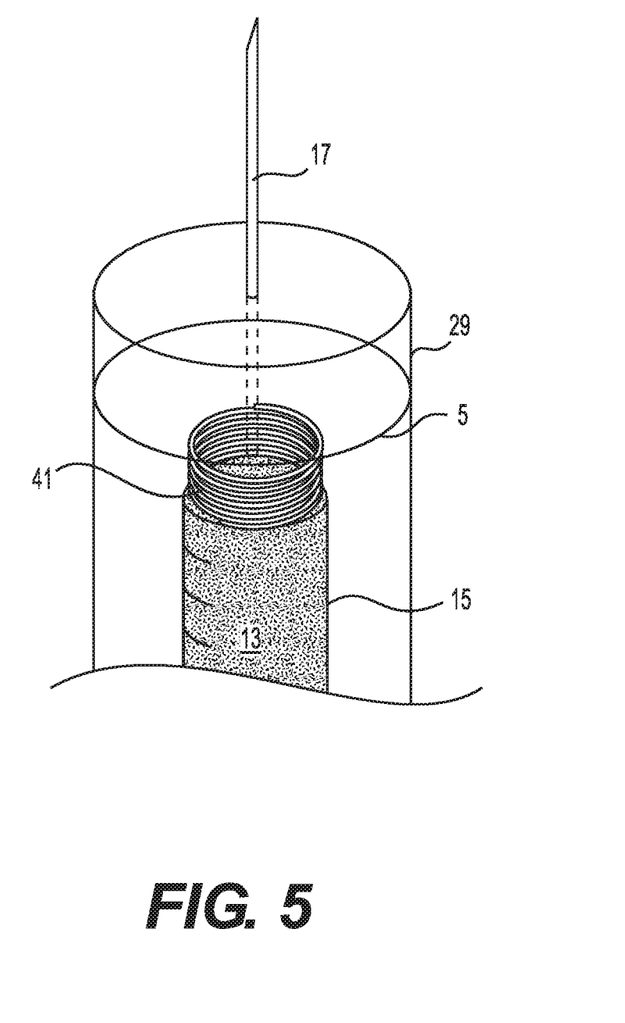
FIG. 5 represents a plan view of an end of an embodiment of an auto-injector including an embodiment of a guide for positioning the needle on a patient's skin prior to administration of medicine.

FIG. 4 illustrates an embodiment of an auto-injector that the patient may utilize to treat the lesion or other skin disorder. Embodiments of an auto-injector 100 typically include a syringe 1. The syringe 1 has a first end 3 and second end 5 and an interior wall 7 and exterior wall 9. The syringe 1 typically includes a space 11 that houses a medicine 13 to be administered. The medicine may be contained by the interior wall 7 of the syringe 1 and other structures described below. Alternatively, the medicine 13 may be contained within a vial 15 arranged in the space 11.

A variety of medicines may be utilized to treat various lesions and skin disorders. For example, an inflamed lesion or other skin disorder may be treated with a solution of and/or a suspension of triamcinolone acetonide (TAC). The strength of the solution may vary depending on the condition and the size of the lesion, among other factors. Typically, the strength of the TAC solution may range from about 2 mg/cc to about 40 mg/cc. Naturally, other medicines may be administered to treat various other dermatological conditions. Additionally, different conditions may require different treatments with other medicines intralesionally. For example, bleomycin may be administered intralesionally to treat viral warts, vascular anomalies, basal cell carcinoma, karatoacanthomas, Kaposi's sarcoma, squamous cell carcinoma, and cutaneous leishmaniasis. Additionally, 5-fluorouracil may be administered intralesionally to treat keloids and squamous cell carcinoma. Furthermore, methotrexate may be administered intralesionally to treat keratoacanthomas. Also, chloroquine may be administered intralesionally to treat chronic discoid lupus erythematosus and sarcoidosis. Still further, interferon may be administered intralesionally to treat lentigo maligna, Peyronie's disease, genital warts, keratoacanthomas and basal cell carcinomas. These are just a few examples of a few conditions and treatment with which the auto-injector may be utilized.

The size of the vial or space to contain medicine may vary, depending upon if the auto-injector is for treating multiple cysts or for carrying out multiple treatments. Along these lines, a single use auto-injector may include a smaller vial or space. An auto-injector may be refillable or the vial replaceable so that the space for medicine or vial need not necessarily be large. An auto-injector for treating multiple lesions or skin disorders may have a larger space for medicine or vial. The range of the amount of TAC solution would be between about 0.1 cc to about 0.5 cc of solution. Other medicants may also be delivered intralesionally. Such medicants may include bleomycin, 5-fluorouracil, methotrexate, chloroquine and interferon. Other conditions that may be treated can include viral warts, keloids, keratoacanthomas and discoid lupus erythematosus. The range of solution that is injected to treat these other conditions may range from about 0.1 cc to about 2 cc administered per treatment.

A needle 17 for delivery of medicine may be arranged at the second end 5 of the syringe 1. The needle 17 may be replaceable or fixed in place. For example, the needle 17 could be similar to a typical needle assembly in a syringe. Alternatively, the needle could be fixed to a cap that is connected to the syringe. Along these lines, the cap could be attached to the syringe with a threaded connection or another connection that could make the cap and needle removable and replaceable. The cap could be permanently adhered to the syringe.

In a disposable auto-injector, the needle and/or cap is typically permanently attached to the syringe. On the other hand, in a reusable auto-injector, the needle and/or needle assembly including the cap may be replaceable. Some embodiments may include a retractable needle. Such embodiments may be disposable or reusable.

The size of the needle typically is sufficient to carry out an intralesional or intradermal injection. This typically will result in the injection of the medicine directly into the lesion or other skin condition. An intramuscular injection, such as carried out for administering a vaccine, is carried out deeper in the skin. Typically, the auto-injector may administer a dose of medicine at a depth of about 3 mm or less. More typically, the auto-injector is configured to administer a dose at a depth of about 1 mm to about 3 mm. Depending on the condition and body area, the healthcare provider may help choose the proper depth on the auto-injector.

Since the patient will carry out the injection, it is important that the needle length be such that the medicine will be correctly administered. The length of the needle is typically from about 4 mm to about 12 mm.

The needle has a thickness, or gauge, to maximize patient comfort. Along these lines, the needle may have a gauge of about 32 to about 34. According to one embodiment, the needle is a 34 gauge needle.

To facilitate injection of the medicine in the proper location, the auto-injector may include an injection guide 29, an embodiment of which is shown in FIG. 4. The guide extends from the second end 5 of the syringe 1 at least as far as the needle. Typically, the guide may extend farther from the second end of the syringe than the needle. The injection guide may extend a distance from the second end of the syringe sufficient to prevent contact of the needle with the skin prior to injection.

The injection guide may help to center the needle over the lesion or other skin disorders prior to injection. Thus, the injection guide may have a round shape. The injection guide may be visually arranged about the perimeter of the lesion or other skin condition and then the injection carried out. The injection guide could have an inner diameter of from about 6 mm to about 10 mm. The size of the injection guide may differ to treat different size lesions or other skin disorders. For example, to treat a small lesion or other skin disorder, the injection guide may have a diameter of about 6 mm. An injection guide having a diameter of about 8 mm may be used to treat a medium size lesion or disorder. For a large lesion or disorder the injection guide may have an inner diameter of about 10 mm. The size of the diameter of the inner wall of the injection guide may be smaller or larger than the dimensions discussed herein.

The injection guide could be formed with the syringe. Alternatively, the injection guide could be permanently or replaceably attached to the second end of the syringe. As such, auto-injectors may be produced having different sized injection guides.

To increase the flexibility of the auto-injector, the injection guide may be replaceable or adjustable. Along these lines, the injection guide may be attachable to the syringe with a connection that permits the injection guide to be removed. The connection could include threads, tabs and guides, indents and protuberances or any other connection that permits changing the injection guide. The guide could also be adjustable, such as including interweaving leaves that can be opened up or closed together, such as a camera diaphragm. A replaceable or adjustable injection guide could have the diameters discussed above.

To carry out the injection, the auto-injector may include a plunger 19 or other structure configured to apply force to the medicine in the syringe or vial through the needle and into the patient. The plunger may be similar to a typical syringe plunger. The plunger is typically arranged in the vicinity of the first end 3 of the syringe 1.

To further customize the auto-injector to provide the most appropriate treatment, the auto-injector may include a selection assembly 21 configured to vary the amount of medicine administered by the auto-injector. The selection assembly 21 may vary the distance that the plunger is advanced and/or vary the amount of medicine administered. The selection assembly may alternatively alter the position at which the plunger is arranged prior to commencing the administration of medicine. Along these lines, prior to placing the auto-injector the plunger may be positioned in the desired position. This may cause some medicine to be ejected from the needle. The selection assembly may alternatively limit depth to which the plunger moves into the syringe during administration of the medicine. The injection may then be carried out.

The embodiment of the selection assembly shown in FIG. 4 includes three dose selectors 23, 25 and 27 configured to administer large, medium and small doses to correspondingly sized lesions or other skin disorders. The embodiment also includes three depth selectors 35, 37, and 39 configured to control the depth to which the needle will extend during administration of the medicine. The dose and depth selectors may be arranged on a side of the auto-injector. The dose selectors in this embodiment may be interconnected with the plunger to control the dose by controlling the depth to which the plunger advances. The depth selector may also control the depth to which the plunger advances. Typical dosage sizes are discussed above. The auto-injector may be configured to permit selection among any therapeutically effective dose or amount. Table 2 below provided examples of diameter of lesions, dose and which lever is actuated.

TABLE 2

Diameter Guide

| Diameter Size | Lesion Dose | Button |
|---|---|---|
| Less than 6 mm | 0.01 cc TAC | S (Small Dose) |
| Between 6-10 mm | 0.02 cc TAC | M (Medium Dose) |
| Greater than 10 mm | 0.03 cc TAC | L (Large Dose) |

Additionally, the auto-injector may be configured to control the depth to which the injection is made. As with the dose size, the depth to which the dose is delivered may depend upon the size of the lesion. The depth could be, for example, from about 1 mm to about 3 mm. The dose of medicine could be delivered at other depths. The embodiment shown in FIG. 4 includes three selectors configured to control the depth to which the medicine is delivered. For example, the selectors could permit arrangement of the needle to administer the medicine at about 1 mm, about 2 mm, or about 3 mm. The depth of delivery could be determined utilizing a measuring grid or by a healthcare provider. There may be one or more structures connecting the plunger to each or all of the selectors.

The height of the lesion may be extrapolated from measuring the diameter of the lesion. For example, a relationship between the diameter determined with the measuring grid on the lesion for height will determine the depth as shown in Table 3 below.

TABLE 3

Height Guide

| Height | Lesion Depth | Button |
|---|---|---|
| Less than 2 mm | 1 mm Deep | 1 |
| Between 2-3 mm | 2 mm Deep | 2 |
| Greater than 3 mm | 3 mm Deep | 3 |

Alternatively, an actuator could be attached to the end of the plunger, similar to a traditional syringe. One or more levers could act as a stop to prevent the plunger from moving beyond a certain point. This would control the amount of medicine forced out of the auto-injector by the plunger.

Some embodiments may include a spring 41 configured to actuate the plunger to administer the medicine. The spring may bias the plunger, vial and needle upward as shown in FIG. 4 such that the needle is concealed within the syringe when not in use. The plunger will act against the spring during administration of the medicine.

The size of the dose may depend upon the medicine, concentration of medicine, condition being treated, size of a lesion, among other factors. The auto-injector may be configured to administer doses of from about 0.01 cc to about 0.03 cc. To treat an inflamed skin lesion, the auto-injector could be configured to administer about 0.01 cc to a small lesion, about 0.02 cc to a medium lesion or about 0.03 cc to a large lesion. Other amounts could also be administered.

The depth to which the medicine is administered may also be varied. This could be accomplished by varying the length of the injection guide and/or varying the length of the needle, for example. As described above and shown in FIG. 4, depth selectors may be included to control a depth to which the plunger may advance and, thus, the depth to which the needle advances from the syringe. Also, depending on the condition being treated, the height of the lesion, and the location on the body the patient can determine the proper depth or a healthcare provider will instruct the patient as to a proper depth.

Figure 6:
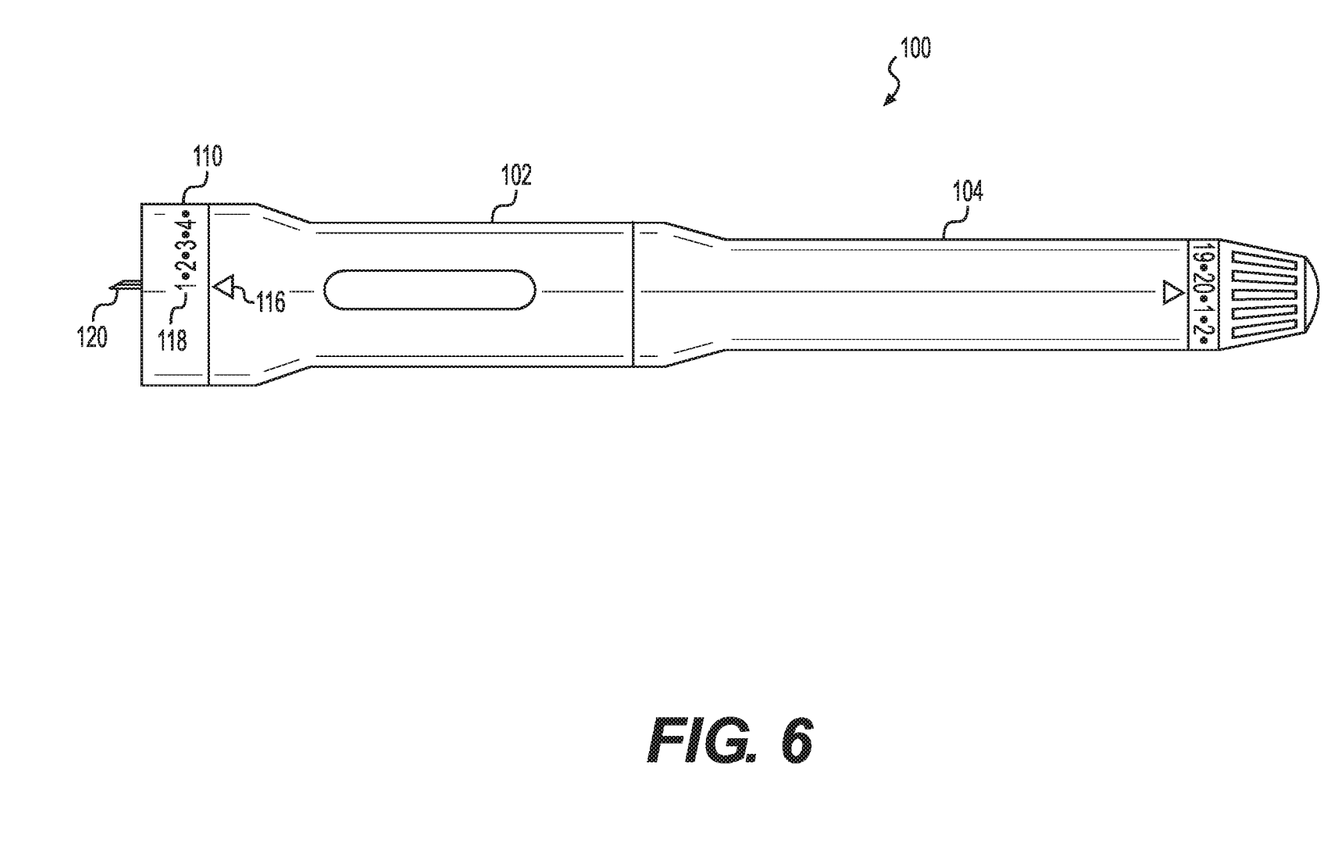
FIG. 6 represents a plan view of another embodiment of an auto-injector.

FIG. 6 illustrates another embodiment of an auto-injector 100. The auto-injector shown in FIG. 6 includes a forward housing element 102 and a rear housing element 104. The forward housing element contains the medicine to be administered and the rear housing the user actuated administration mechanism. The two housing elements may be connected together with a threaded connection 106 and 108. According to some embodiments, the housing elements may be integral or other connections may be utilized. One advantage of a separable connection, such as a threaded connection is that the medicine, needle and other elements may be replaceable.

A first end of the forward housing element includes a depth selector 110. The embodiment of the depth selector shown in FIG. 6 may be rotated to change the extent to which the needle 120 extends from the auto-injector. The embodiment of the depth selector shown in FIG. 6 is connected to the forward housing with a threaded connection 112 and 114. Other connections may also be utilized. A separable connection may be advantageous to permit replacement of the needle.

Indicators 116 on the forward housing and 118 on the depth selector permit the user to select the depth to which the needle 120 will penetrate the user's skin. The embodiment of the depth selector shown in FIG. 6 permits the needle to be adjusted to three depths. The depth selector and/or the forward housing may include one or more detents and complementary protrusions or other elements to indicate when a certain depth has been selected and/or to maintain the depth selector and needle in the selected position.

The needle 120 may be part of a needle assembly including a needle base 122 in which the needle may be anchored. A needle guide 124 may be included to guide the needle during administration. The needle guide may also help to prevent bending of the needle during administration, particularly as the needle penetrates the skin. Along these lines, the needle guide may include a tip 126 having an inner diameter slightly wider than the exterior diameter of the needle.

The adjustment of the depth with the depth adjuster may advance the needle guide. Along these lines, the exterior surface of the needle guide may abut the interior of the depth adjuster or the passage 103 in the depth adjuster. If the depth selector is attached to the housing with a threaded connection, as the depth adjuster is screwed or unscrewed, the distance between the distance selector and housing may decrease or increase, respectively. This may advance and withdraw the needle guide and, hence, the needle.

Figure 7:
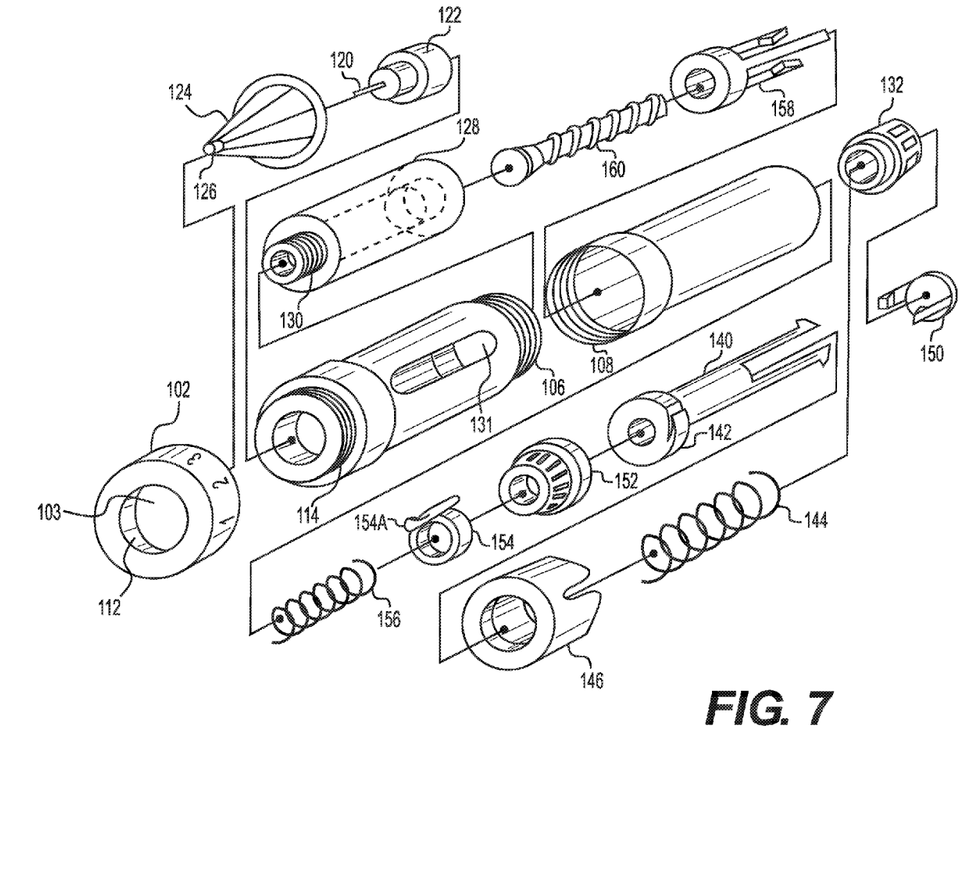
FIG. 7 represents an exploded view of the embodiment shown in FIG. 6.

In the embodiment shown in FIGS. 6 and 7, the forward housing 102 contains the medicine vial 128. The vial may include a threaded connection 130 for connecting the needle base to the vial. The housing 102 may include a cut out or window 131 to facilitate a visual determination of the amount of medicine in the vial.

The end of the rear housing includes a dosage adjuster 132. The dosage adjuster includes indicators 134 to select a dosage. The dosage selected is indicated by an arrow 138 on the housing. The dosage adjuster is connected to a drive sleeve 140. The drive sleeve includes a ratchet mechanism 142 that only permits rotation in one direction with respect to reset ring 152. Each click of the ratchet mechanism corresponds to an increase in the dosage.

Torque is applied to a spring 144 as the dosage adjuster is turned. Spring 144 is secured to drive sleeve 140 with a spring holder 146. The spring holder engages the end of the spring and abuts the ratchet mechanism 142, thereby permitting torque to be applied to the spring 144. On the other hand, spring 156 maintains a forward force on the plunger, vial and needle. Guide 154 may include a guide leg 154a that can slide in slots in the reset ring 152.

Once the desired dose is selected and the springs and other elements set, actuator 150 is pressed by the user. Actuation releases the springs and other elements such that the desired dosage is delivered from the vial at the depth selected with the depth selector.

Figure 8:
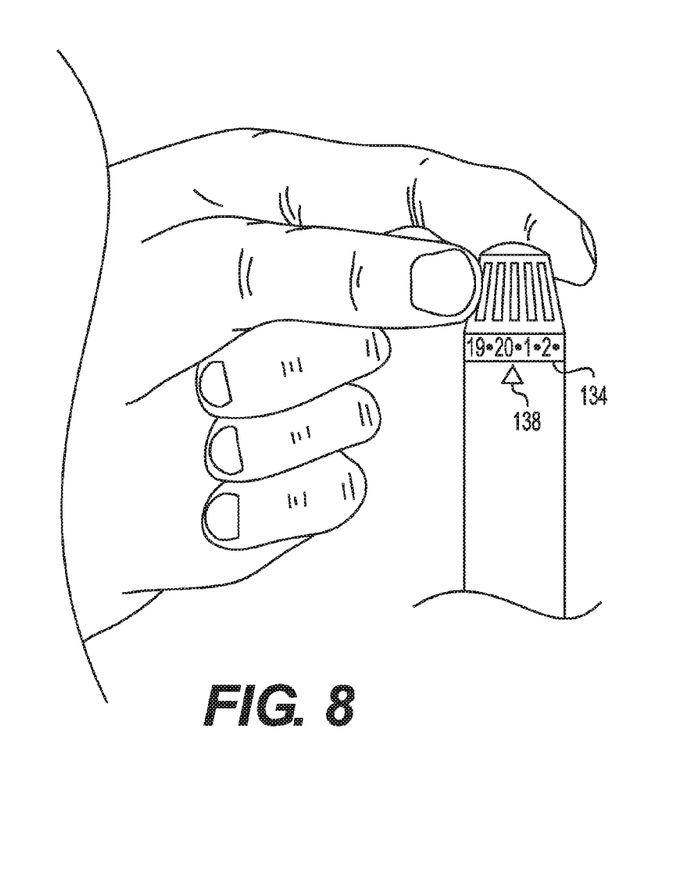
FIGS. 8 and 9 represent views of the embodiment shown in FIGS. 6 and 7 during use.
Figure 9:
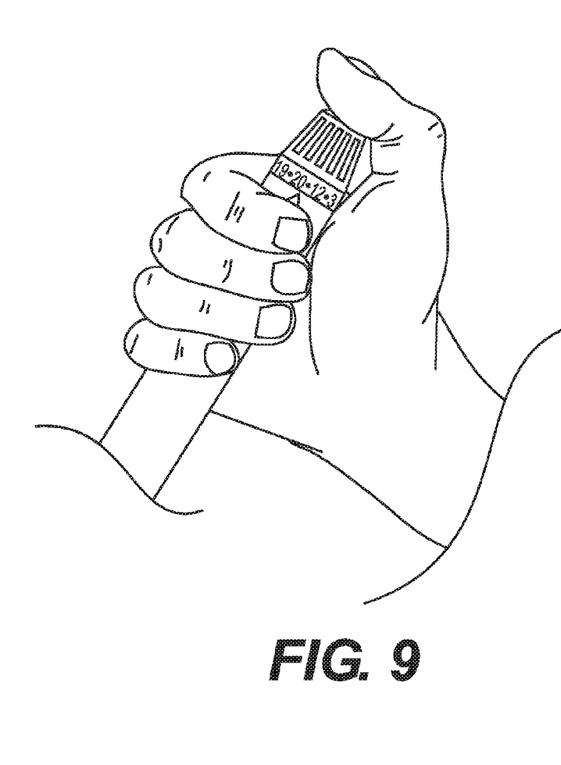

Once the user has selected the desired dose the user places the needle into user's skin and presses down on the actuator 150. The actuator releases the ratchet mechanism and allows the ratchet mechanism to rotate. This rotational energy is provided by the torsion spring 144. Rotation caused by the spring 144 ultimately causes the plunger 160 to advance through the medicine vial, thereby dispensing the medicine. As the threaded plunger 160 advances, a complementarily threaded nut 158 advances on the threaded plunger. When the threaded nut reaches the end of the threaded plunger, the dosage selector cannot be spun any further, indicating that the amount of medicine remaining in the vial is what is displayed on the dial. This may prevent accidental under dosing.

Figure 10:
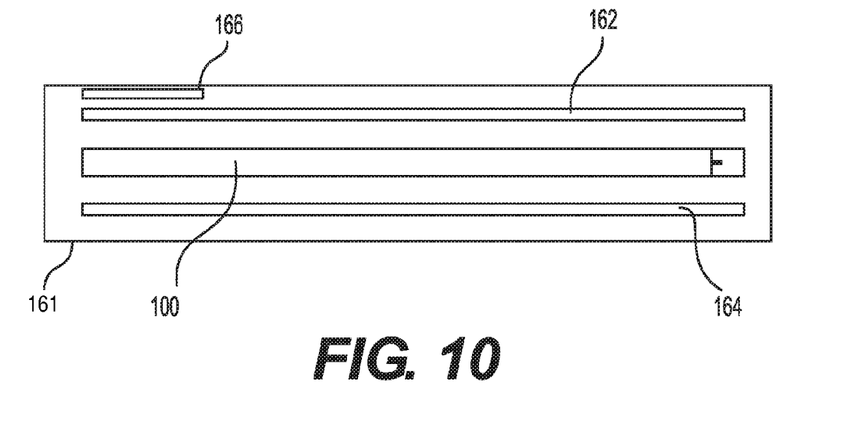
FIG. 10 represents an embodiment of an auto-injector kit.

To facilitate treatment, the auto-injector may be included in a treatment kit 161, an embodiment of which is shown in FIG. 10. The kit may include an antiseptic wipe or swab 162 for disinfecting the injection site. The antiseptic wipe could be made of a woven or unwoven material, such as fabric gauze or a paper. The wipe could include any suitable antiseptic material, such as alcohol or an antibacterial substance. The wipe or swab may be packaged separately. The kit may also include the auto-injector 100, as described herein. Additionally, the kit may include an antiseptic wipe or swab 164 to treat the injection site after the injection. Treating the injection site after the injection may help to prevent bacteria from entering the injection site and remove any blood, pus or other fluids leaking from the injection site. Furthermore, the kit may include a bandage 166 to cover the injection site.

A housing or enclosure could contain all of the elements of the kit. The housing could also receive the auto-injector and any wipes after use, facilitating disposal of the elements of the kit. Along these lines, the auto-injector may be considered medical waste, which requires a particular disposal method. The housing could include a seal to maintain the elements of the kit in a sterile condition. The auto-injector alone may additionally or alternatively include its own seal or enclosure or housing, whether included in a kit or on its own. The seal on a kit or the auto-injector may be breached to gain access to the elements of the kit or the auto-injector. The enclosure may include a simple wrap about the auto-injector alone together with other possible elements of the kit. Each element of the kit may include a separate housing, enclosure, wrapping or packaging. The housing or enclosure may include one or more closure or sealing elements to close the housing or enclosure after carrying out an injection and placing the used elements of the kit back into the housing or enclosure.

Typically, use of the kit includes opening the housing, enclosure, wrapping or packaging. If the kit includes a pre-injection wipe, then the wipe may be retrieved from any housing, enclosure, wrapping or packaging and the potential injection site cleaned. The auto-injector may be removed from any housing, enclosure, wrapping or packaging and configured for injection as described above. The injection may then be carried out. A post-injection wipe may be retrieved from any housing, enclosure, wrapping or packaging and the injection site cleaned. The auto-injector and wipes may be disposed of. According to some embodiments, the auto-injector and possibly a pre-injection and/or post injection wipe may be reintroduced into a housing, enclosure, wrapping or packaging, the housing, enclosure, wrapping or packaging closed and the used auto-injector and possibly wipes disposed of, such as in a "sharps" or other medical waste container.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

The invention claimed is:

1. An auto-injector device, comprising: a syringe;
  a needle arranged in the vicinity of a first end of the syringe;
  a plunger arranged within the syringe, wherein a volume within the syringe between the plunger and the needle accommodates medicine, such that movement of the plunger toward the needle dispenses an amount of the medicine through the needle;
  a measurement guide having indicia configured to measure one or more dimensions of multiple skin lesions or skin disorders of various sizes; and
  a selection assembly configurable by a user to adjust the amount of medicine dispensed by the auto-injector device and a depth to which the medicine is administered, the selection assembly having selectors directly corresponding to different measurements from the indicia,
  wherein the selectors are selectively operable by the user and configured to adjust the amount and the depth based on a size of a skin lesion or a skin disorder.

2. The auto-injector device according to claim 1, further comprising:
an injection guide extending from the first end of the syringe, the injection guide configured to center the needle with respect to an injection site on the user.

3. The auto-injector device according to claim 1, further comprising:
a replaceable vial containing the medicine, wherein the medicine is dispensed from the vial by the plunger through the needle.

4. The auto-injector device according to claim 1, wherein the selection assembly is configured to limit a depth to which the plunger moves in the syringe.

5. The auto-injector device according to claim 1, wherein the auto-injector is disposable and configured for a single use.

6. The auto-injector device according to claim 1, wherein the auto-injector is configured for multiple uses.

7. The auto-injector device according to claim 1, wherein selection assembly is configured to administer doses of about 0.01 cc, about 0.02 cc or about 0.03 cc.

8. The auto-injector device according to claim 1, wherein the needle is configured to administer a dose at a depth of about 1 mm to about 3 mm.

9. The auto-injector device according to claim 1, wherein the selection assembly is configured to adjust a volume of dosage to be administered and a depth to which the dosage is administered.

10. The auto-injector device according to claim 9, wherein the selection assembly is configured to increase a depth to which the medicine is administered as the dosage of the medicine increases.

11. The auto-injector device according to claim 1, wherein the selection assembly comprises a plurality of dosage selector buttons configured to cause the auto-injector to administer a plurality of different dosages of medicine, and a plurality of depth selector buttons configured to adjust the depth to which the medicine is administered by the auto-injector.

12. The auto-injector device according to claim 1, further comprising:
a spring configured to actuate the plunger to administer the medicine.

13. The auto-injector device according to claim 1, wherein the auto-injector is configured to administer a therapeutically effective dose to treat inflamed acne cysts, inflamed sebaceous cysts, bug bites, alopecia areata, hypertrophic scars, keloids, psoriasis, granuloma annulare, discoid lupus erythematosus, hypertrophic lichen planus, lichen planopilaris, lichen simplex chronicus, erythema nodusum, sarcoidosis, and prurigo nodularis.

14. The auto-injector device according to claim 1,
wherein the indicia of the measurement guide are configured to measure a diameter of the skin lesion or the skin disorder, and
wherein the selection assembly is configurable by the user to adjust the amount of medicine via the selectors based on the diameter of a skin lesion or a skin disorder.

15. The auto-injector device accordingly to claim 14, wherein the measurement guide includes a measuring grid comprising a plurality of openings, the openings having varying diameters, and
wherein one of the openings with a diameter corresponding to the diameter of the skin lesion or the skin disorder is capable of being placed by the user over the skin lesion or the skin disorder to measure the diameter of the skin lesion or the skin disorder.

16. The auto-injector device according to claim 1, wherein the selection assembly is configurable by the user to adjust a depth to which the plunger moves in the syringe and thereby to adjust the amount of medicine dispensed by the auto-injector device.

17. The auto-injector device according to claim 2,
wherein the injection guide extends from the first end of the syringe at least as far as the needle.

18. The auto-injector device according to claim 1, further comprising:
a vial containing a medicine.

* * * * *